United States Patent
Schumann et al.

(10) Patent No.: US 12,402,957 B2
(45) Date of Patent: Sep. 2, 2025

(54) INSTRUMENT CALIBRATION

(71) Applicant: DePuy Synthes Products, Inc., Raynham, MA (US)

(72) Inventors: Steffen Schumann, Zofingen (CH); Marc Puls, Thörigen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/488,528

(22) Filed: Oct. 17, 2023

(65) Prior Publication Data

US 2024/0041538 A1 Feb. 8, 2024

Related U.S. Application Data

(63) Continuation of application No. 16/453,710, filed on Jun. 26, 2019, now Pat. No. 11,839,434.

(51) Int. Cl.
*A61B 34/20* (2016.01)
*A61B 17/16* (2006.01)
(Continued)

(52) U.S. Cl.
CPC .......... *A61B 34/20* (2016.02); *A61B 17/1671* (2013.01); *A61B 17/7082* (2013.01);
(Continued)

(58) Field of Classification Search
CPC .. A61B 2560/0238; A61B 2017/00725; A61B 2034/207; A61B 2034/2046; A61B 2034/2068
See application file for complete search history.

(56) References Cited

U.S. PATENT DOCUMENTS

| | | | | |
|---|---|---|---|---|
| 6,497,134 B1 * | 12/2002 | Faul | ............... | A61B 90/36 73/1.79 |
| 6,511,418 B2 * | 1/2003 | Shahidi | ............... | A61B 5/064 73/1.79 |

(Continued)

FOREIGN PATENT DOCUMENTS

| | | |
|---|---|---|
| CN | 1511249 A | 7/2004 |
| CN | 103732165 A | 4/2014 |

(Continued)

OTHER PUBLICATIONS

International Search Report and Written Opinion for Application No. PCT/IB2020/055335, mailed on Aug. 24, 2020, 11 pages.

(Continued)

*Primary Examiner* — Oommen Jacob
(74) *Attorney, Agent, or Firm* — Barnes & Thornburg LLP

(57) ABSTRACT

Surgical instrument calibration methods, systems, and devices are provided that allow a virtual representation of a surgical instrument to be modified to adjust for any variations in a distal tip of a surgical instrument. For example, an instrument calibration system is provided that can have a surgical instrument, a calibration instrument, and a monitoring system. The surgical instrument can have a distal tip and an orientation element thereon, and the calibration instrument can have a pivot point thereon and a calibration reference element attached thereto. The monitoring system can be configured to record movement of the surgical instrument with respect to the calibration instrument when the tip of the surgical instrument is inserted into the pivot point of the calibration instrument, and to calculate a deviation of the tip of the surgical instrument from a predefined ideal tip based on the recorded movement.

12 Claims, 13 Drawing Sheets

(51) Int. Cl.
  *A61B 17/70* (2006.01)
  *A61B 34/00* (2016.01)
  *A61B 34/30* (2016.01)
  *G16H 40/40* (2018.01)
(52) U.S. Cl.
  CPC .............. *A61B 34/25* (2016.02); *A61B 34/30* (2016.02); *G16H 40/40* (2018.01); *A61B 2034/2048* (2016.02); *A61B 2034/2051* (2016.02); *A61B 2034/2055* (2016.02); *A61B 2034/2072* (2016.02); *A61B 2034/254* (2016.02); *A61B 2560/0238* (2013.01)

(56) References Cited

U.S. PATENT DOCUMENTS

| | | | |
|---|---|---|---|
| 11,839,434 | B2 | 12/2023 | Schumann et al. |
| 2004/0044295 | A1* | 3/2004 | Reinert .................. G16H 20/40 600/587 |
| 2004/0158260 | A1* | 8/2004 | Blau ...................... A61B 90/36 606/108 |
| 2004/0167654 | A1* | 8/2004 | Grimm .................. A61B 34/20 700/114 |
| 2005/0267358 | A1 | 12/2005 | Tuma et al. |
| 2008/0228195 | A1* | 9/2008 | von Jako .............. A61B 34/20 606/130 |
| 2009/0163930 | A1* | 6/2009 | Aoude ................... A61B 34/20 606/130 |
| 2009/0171197 | A1* | 7/2009 | Burger .................. A61B 34/20 600/426 |
| 2009/0202387 | A1 | 8/2009 | Dlugos, Jr. et al. |
| 2009/0326324 | A1* | 12/2009 | Munoz Martinez ... A61B 34/30 901/30 |
| 2010/0331855 | A1* | 12/2010 | Zhao ..................... A61B 34/30 606/130 |
| 2015/0182293 | A1* | 7/2015 | Yang .................. A61B 17/1703 600/424 |
| 2017/0345177 | A1 | 11/2017 | Hladio et al. |
| 2018/0140223 | A1 | 5/2018 | Kheradpir et al. |
| 2019/0029765 | A1 | 1/2019 | Crawford et al. |
| 2020/0405400 | A1* | 12/2020 | Schumann ............. A61B 34/20 |
| 2024/0041538 | A1* | 2/2024 | Schumann ......... A61B 17/1671 |

FOREIGN PATENT DOCUMENTS

| | | |
|---|---|---|
| CN | 109171962 A | 1/2019 |
| JP | 2003534035 A | 11/2003 |
| JP | 2009254805 A | 11/2009 |
| WO | 0167979 A1 | 9/2001 |
| WO | 02061371 A1 | 8/2002 |
| WO | 2010077008 A2 | 7/2010 |
| WO | 2017200445 A1 | 11/2017 |

OTHER PUBLICATIONS

Koulechov, Kirill (2006) "Leistungssteuerung chirurgischer Instrumente in der Kopf-Chirurgie", "Performance control of surgical instruments in head surgery", Technical University of Munich, Munich, Germany, 156 pages.

* cited by examiner

INSTRUMENT CALIBRATION

CROSS REFERENCE TO RELATED APPLICATION

This application is a continuation of U.S. patent application Ser. No. 16/453,710, filed Jun. 26, 2019 and entitled "INSTRUMENT CALIBRATION," which is hereby incorporated by reference herein in its entirety.

FIELD

Surgical devices, systems, and methods are provided for performing instrument calibration on surgical instruments.

BACKGROUND

Computer and/or robotic-assisted surgery has allowed for more successful surgical outcomes by providing a variety of different benefits to a surgeon, such as improved visualization during surgery, guidance, better control over instruments, etc. For computer and/or robotic systems to provide assistance, navigation systems are used for tracking movements of surgical instruments during a procedure and providing a virtual representation of the instrument relative to a scan of the patient. Accurately tracking movements of the instruments and accurately representing the instruments in various virtual representation is important for the safety of the patient. As such prior to use, each instrument must be calibrated to ensure accurate measurements and accurate virtual representations. However, current methods present challenges, such as accurately modeling instruments.

Therefore, improved instrument calibration techniques are needed.

SUMMARY

Methods, devices, and systems are provided herein that allow an instrument to be calibrated such that a virtual representation of the instrument can be updated to accommodate for any distortions or bending that may occur at the distal tip over time, such as in instruments having a curved distal tip. In one aspect, an instrument calibration system is provided with a surgical instrument that has an elongate shaft with a proximal end and a distal end. The distal end has a distal-most tip while the proximal end has an orientation element fixed in an initial position thereon. The system also has a calibration instrument with a point thereon that is configured to receive the distal-most tip of the surgical instrument for pivoting thereabout. The calibration instrument also has a predefined geometric structure and a calibration reference element attached thereto. The system also has a monitoring system that is configured to record movement of the surgical instrument when the distal-most tip of the surgical instrument is positioned at the pivot point of the calibration instrument by recording a relative position of the orientation element to the calibration reference element. The monitoring system is configured to calculate a deviation of the distal-most tip of the surgical instrument from a predefined ideal distal-most tip based on the recorded movement of the orientation element of the surgical instrument, a predefined ideal instrument axis of the surgical instrument, and the predefined ideal distal-most tip of the surgical instrument, and the monitoring system is configured to modify a virtual representation of the surgical instrument on a display based on the calculated deviation.

The system can have numerous variations. For example, the distal end of the surgical instrument can be a curved tip. In another example, the distal end of the surgical instrument can have a cavity formed therein. In one example, the monitoring system can be configured to determine an initial orientation of the orientation element with respect to the surgical instrument while the orientation element remains in a fixed position relative to the surgical instrument. In another example, the monitoring system can be configured to determine an actual orientation of the surgical instrument in use while the orientation element on the proximal end thereof is moved to one of a plurality of second positions different than the initial position on the surgical instrument without requiring re-recording movement of the surgical instrument with respect to the calibration instrument.

In still another example, the pivot point on the calibration instrument can include a plurality of removable and replaceable pivot points, and each of the plurality of removable and replaceable pivot points can be configured to correspond to one of a plurality of different distal-most tips of a plurality of different surgical instruments. The monitoring system can also be configured to be updated depending on which one of the plurality of removable and replaceable pivot points is used.

In some embodiments, each of the orientation element and the calibration reference element can include one of an array having a plurality of trackable targets thereon, an electro-magnetic sensor, and a gyroscope. The monitoring system can also include at least one camera, at least one sensor, at least one processor, and at least one display. In some embodiments, the monitoring system can be part of a robotic surgery system, and the surgical instrument can be configured to be controlled by the robotic surgery system. Exemplary surgical instruments include, for example, a screwdriver and a discectomy device. In another embodiment, the orientation element can be configured to rotate about the surgical instrument in a plurality of known orientations, and the monitoring system can be configured to update a virtual representation of the surgical instrument on a display based on each of the plurality of known orientations of the orientation element without rerecording the relative position of the orientation element to the calibration reference element in each of the plurality of known orientations.

In another aspect, a method of calibrating a surgical instrument for use during surgical navigation is provided that includes inserting a distal-most tip on a distal end of the surgical instrument onto a pivot point on a calibration instrument while the calibration instrument has a predefined geometric structure and a calibration reference element attached thereto. The method also includes pivoting the surgical instrument about the pivot point such that a proximal end of the surgical instrument moves along an approximately circular path above the calibration instrument while a monitoring system records reference coordinate points of an orientation element fixed at a first position on the surgical instrument relative to reference coordinate points of the calibration reference element on the calibration instrument. The method further includes comparing, by the monitoring system, the recorded reference coordinate points to at least one stored reference coordinate point of an orientation element on a predefined ideal surgical instrument to calculate a deviation of the distal-most tip of the surgical instrument from a predefined ideal distal-most tip based on the comparison. After determining the deviation of the distal-most tip, the monitoring system modifies a virtual representation of the surgical instrument on a display based on the calculated deviation.

The method can have a number of variations. For example, the method can include determining by the monitoring system an initial orientation of the orientation element with respect to the surgical instrument while the orientation element remains in a fixed position relative to the surgical instrument.

In another embodiment, the pivot point can be formed on a removable portion of the calibration instrument, and the method can include replacing the removable portion of the calibration instrument with a second removable portion having a second pivot point with a different shape configured to match the distal-most tip of the surgical instrument. In some embodiments, the method can include updating the monitoring system based on the second pivot point.

In other aspects, the method can include, after modifying the virtual representation of the surgical instrument based on the calculated deviation, rotating the orientation element of the surgical instrument to a different known orientation and modifying by the monitoring system the virtual representation of the surgical instrument on the display based on the different known orientation of the orientation element.

In another aspect, a method for calibrating a surgical instrument with a distal-most tip is provided that includes recording, by a monitoring system, a movement of an orientation element at an initial position on the surgical instrument with respect to a calibration reference element on a calibration instrument. The method also includes calculating, by a processor operatively coupled to the monitoring system, a deviation of the distal-most tip of the surgical instrument from a predefined virtual representation of the distal-most tip of the surgical instrument by comparing the recorded movement of the orientation element of the surgical instrument to an expected movement of the orientation element. The predefined virtual representation of the distal-most tip of the surgical instrument includes a plurality of data points stored in a memory accessible by the processor that define a representation of the surgical instrument. The method also includes updating, by the processor, one or more first data points stored in the memory among the plurality of data points of the predefined virtual representation of the distal-most tip of the surgical instrument based on the calculated deviation of the distal-most tip.

Multiple variations of the method are possible. For example, the method can include controlling, by the processor, a surgical display so as to display the one or more updated first data points of the predefined virtual representation of the distal-most tip of the surgical instrument. In another example, the method can include, after updating the one or more first data points, determining, by the processor, an orientation of the surgical instrument during use when the orientation element thereon is moved to a second position different than the initial position on the surgical instrument without re-recording the movement of the surgical instrument with respect to the calibration instrument. In such an example, the method can also include updating, by the processor, one or more second data points stored in the memory among the plurality of data points of the predefined virtual representation of the distal-most tip of the surgical instrument based on the second position of the orientation element.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
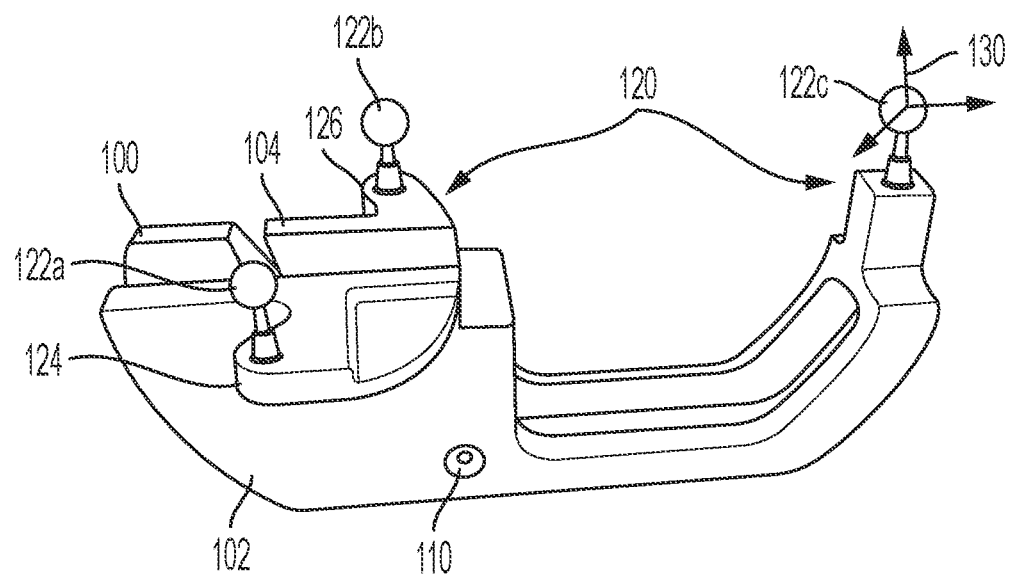
FIG. 1 is a perspective view of one embodiment of a calibration instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, devices, and systems are provided for performing instrument calibration on surgical instruments with curved distal tips. During computer and/or robotic-assisted surgery, an accurate virtual representation of any instrument being used during surgery is needed for the computer or robotic system to be able to correctly assess a current location of the instrument and to correctly provide assistance, guidance, etc. to the surgeon. Because virtual representations of instruments with curved distal tips can become inaccurate as a result of an actual distal tip on a corresponding surgical instrument bending or warping over time, updating a virtual representation of an instrument with a curved distal tip so that it accurately reflects a current distal tip geometry of the instrument can allow for better surgical results. For example, the virtual representation used by the computer or robotic system can accurately reflect the instrument used in the surgery rather than the system having to assume a distal tip is in an ideal state. Additionally, it can allow for reduced waste by eliminating the need to discard any surgical instrument that cannot be calibrated only because the curved distal tip is not in a perfect or near-perfect state while the instrument is otherwise surgically acceptable. Thus, instruments with curved tips can be accurately calibrated using the methods, devices, and systems provided herein such that a computer or robotic system can determine accurate distal tip geometry and measurements of the instruments, even after repeated use, and accurately update a virtual representation of the instrument.

Instrument calibration can be performed on a surgical instrument with a curved distal tip using a navigation array fixed on the surgical instrument in a first orientation. In certain embodiments, the navigation array can be rotated and/or moved into one or more different orientations on the surgical instrument during use to ensure the surgical instrument can be continually tracked by the computer or robotic system without requiring the surgical instrument to be recalibrated each time an orientation of the navigation array is changed. This movement allows the surgeon more flexibility in rotating or maneuvering the surgical instrument during use while saving time and still ensuring that the instrument is tracked by the system.

An exemplary instrument calibration system can include a surgical instrument with an elongate shaft that has a curved distal tip and an orientation array thereon. A calibration instrument can also be provided that has a predefined geometric structure and a calibration reference array attached thereto. A pivot point can be formed in the calibration instrument that is configured to receive the curved distal tip of the instrument. A monitoring system can also be provided that is configured to record coordinates of the surgical instrument when the curved distal tip of the surgical instrument is inserted into the pivot point of the calibration instrument and the instrument is rotated thereabout. Based on the recorded coordinates, the monitoring system can be configured to calculate a deviation of the curved distal tip of the surgical instrument from a predefined ideal curved tip and modify a virtual representation of the surgical instrument on a display based on the calculated deviation such that the virtual representation accurately mirrors the actual curved distal tip of the instrument with any bends or deviations reflected therein. Virtual representations can include a variety of different information and/or data representing parts of the instruments and systems discussed herein. For example, virtual representations can include pluralities of data points defining and/or representing shapes, orientations, locations, etc. of the various components of the systems discussed herein.

FIG. 1 illustrates one exemplary embodiment of a calibration instrument 100 with a pivot point 110 formed therein and a calibration reference array 120 attached thereon. The calibration instrument 100 is configured to allow calibration of a surgical instrument 200 with a curved distal tip 210 by a monitoring system 300, discussed in detail below. The calibration instrument 100 has a predefined side and shape that is known to the monitoring system 300, and the pivot point 110 is formed in one side 102 thereof.

Figure 2A:
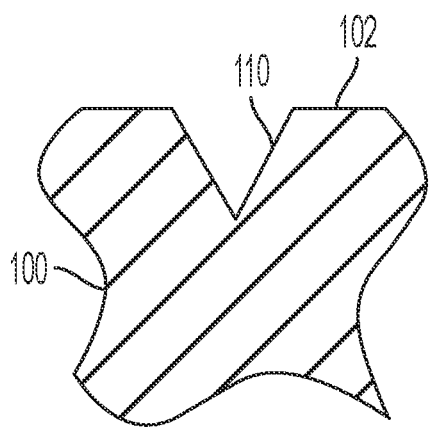
FIG. 2A is a cross-sectional side view of a pivot point in the calibration instrument of FIG. 1.
Figure 2B:
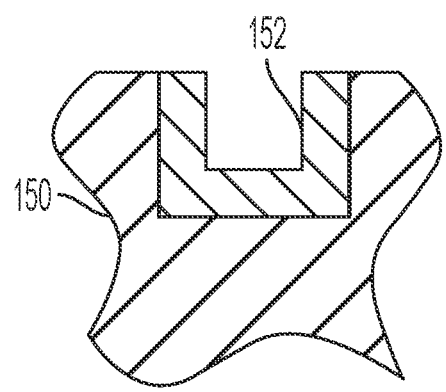
FIG. 2B is a cross-sectional side view of a pivot point in another embodiment of a calibration instrument similar to the calibration instrument of FIG. 1.

The pivot point 110 is configured to receive the curved distal tip 410 of the surgical instrument 200 therein. The pivot point 110 can be sized and shaped to complement the curved distal tip 210 and to provide a relatively secure hold on a distal-most end 212 of the curved distal tip 210 to prevent the distal tip 210 from sliding around in the pivot point 110. At the same time, the pivot point 210 provides a fixed point about which the surgical instrument 200 can smoothly rotate or pivot, as discussed more below. Thus, the pivot point 110 can be specifically configured to receive distal tips of certain instruments or groups of instruments, and dimensions of the pivot point 110 like depth of the cavity, diameter of the circular opening on the side wall 102, angles of the sidewalls of the cavity, etc. can all be varied. For example, the pivot point 110 can be a cavity shaped like an inverse cone, as illustrated in FIG. 2A, for receiving a cone-shaped or more rounded tip. However different embodiments can have different shaped pivot points depending on the type of distal end being received therein, such as cavities shaped like inverse cylinders, spheres pyramids, prisms, etc. While the pivot point 110 is formed in one side 102 of the calibration instrument 100, it can be formed in various other locations on the calibration instrument 100 in other embodiments. Additionally, in some embodiments, the pivot point 110 can be removable and replaceable to allow different pivot points configured to accept different types of distal tips to be inserted and used during calibration of different types of instruments. For example, FIG. 2B illustrates a removable pivot point mechanism 152 that can be inserted into and removed from a calibration instrument 150 that is similar to the instrument 100, and the removable pivot point mechanism 152 can be secured in place through a variety of different means, such as through clips, engagements, friction, etc.

The calibration instrument 100 also has a calibration reference array 120 attached thereto that is configured to be tracked by the monitoring system 300. The calibration reference array 120 has a predefined arrangement known to the monitoring system 300 such that it can provide a predefined 3-dimensional calibration coordinate system 130 to the monitoring system 300 during calibration. For example, as the instrument 200 is calibrated by pivoting the instrument 200 relative to the pivot point 110, the calibration reference array 120 is configured to allow the monitoring system 300 to take images containing the calibration reference array 120. Because the dimensional arrangement and orientation of the calibration reference array 120 with respect to itself and the calibration instrument 100 is predefined and known to the monitoring system 300, the calibration reference array 120 allows the monitoring system 300 to use the calibration reference array 120 in each image as a reference scale to determine various orientation and measurement values of other objects in the images based on the position and visibility of the calibration reference array 120 in each image. This allows the monitoring system 300 to effectively place other objects in the images to scale within the context of the calibration coordinate system 130.

Figure 10:
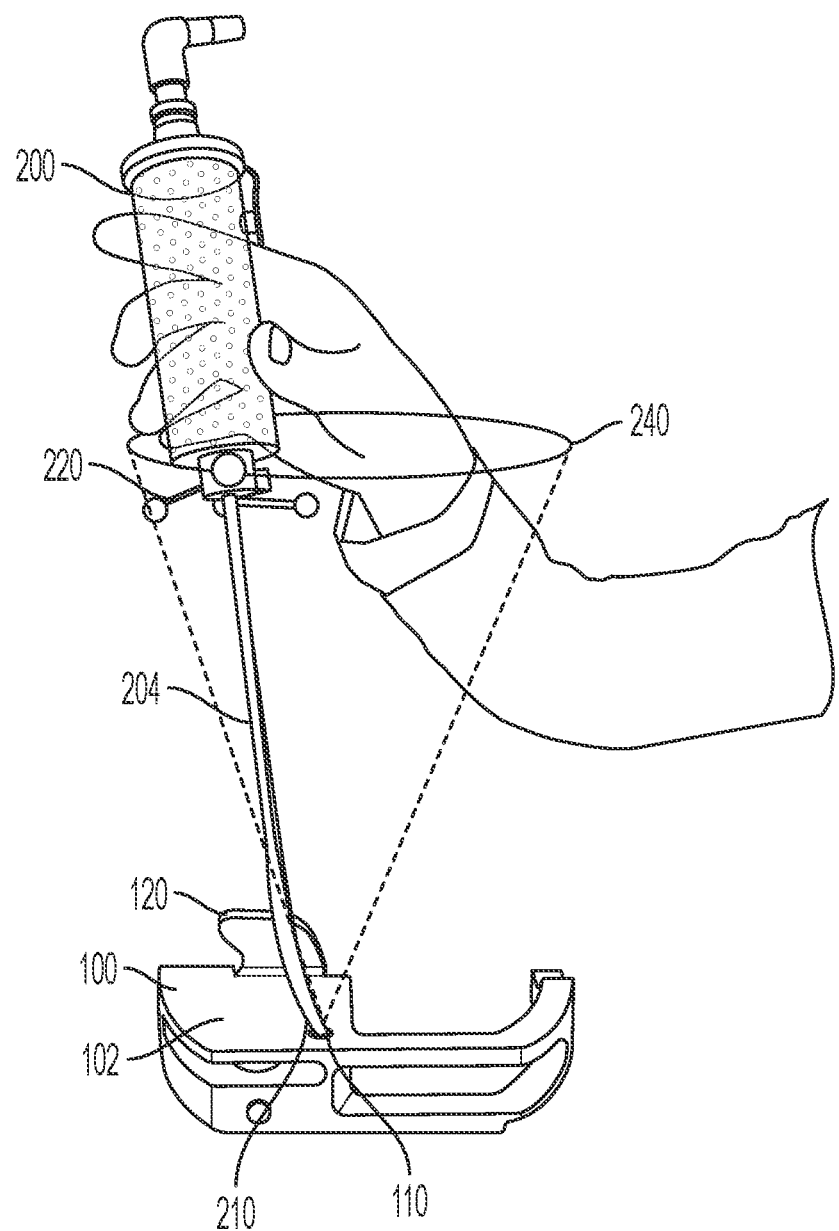
FIG. 10 is a perspective view of the calibration process of FIGS. 7 and 8 with the surgical instrument of FIG. 3 rotating with respect to the calibration instrument of FIG. 1.
Figure 11:
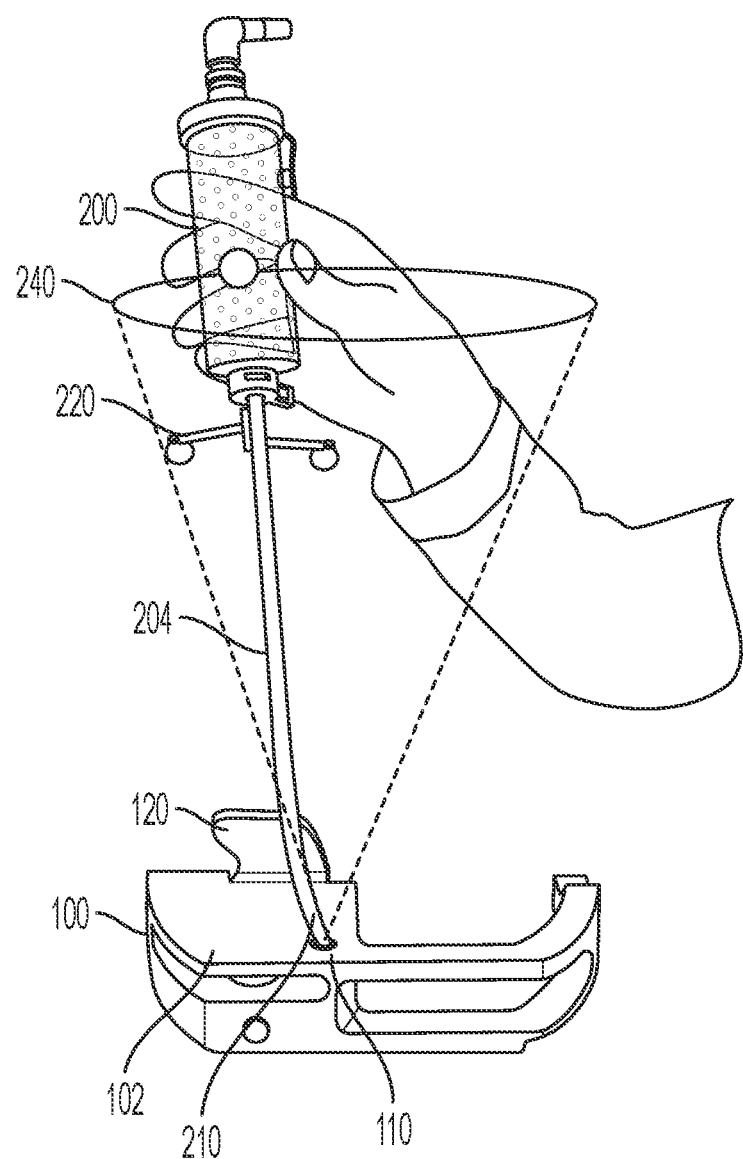
FIG. 11 is a perspective view of continued rotation of the surgical instrument and the calibration instrument in FIG. 10.
Figure 12:
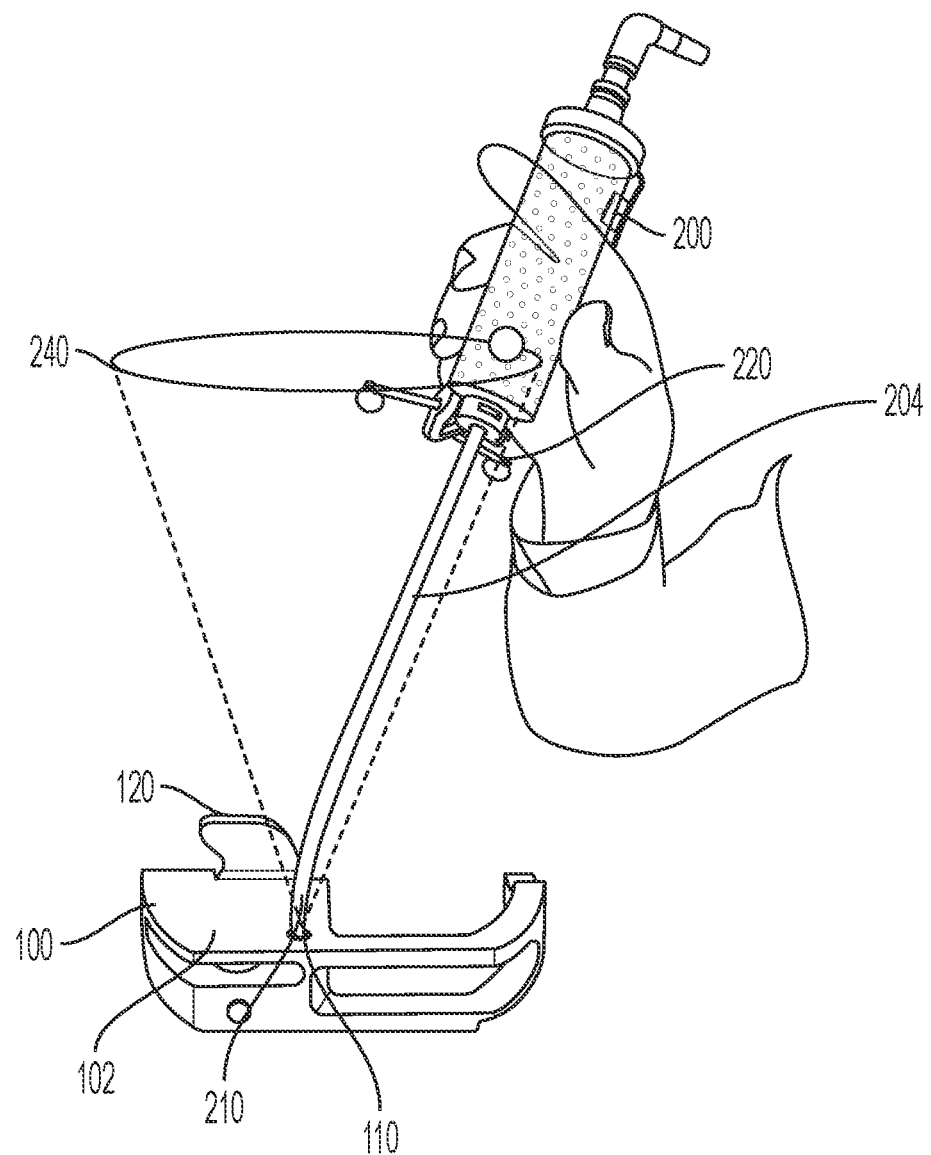
FIG. 12 is a perspective view of continued rotation of the surgical instrument and the calibration instrument in FIG. 11.

The illustrated calibration reference array 120 has three targets 122a, 122b, 122c thereon that can be imaged and tracked by the monitoring system 300 to provide a calibration coordinate system 130 to the monitoring system 300 and/or the control system 400. The targets 122a, 122b, 122c are arranged in a generally triangular configuration in a single plane that extends parallel to and above an upper surface 104 of the calibration instrument 100. Targets 122a, 122b are arranged on wings 124, 126 that extend laterally away from each other on the upper surface 104 of the calibration instrument 100. The calibration instrument 100 can be tipped sideways to rest on the wing 126 and maintain the calibration instrument 100 at a defined and consistent angle. During calibration, the pivot point 110 is thus accessible so that a distal tip of the instrument 200 can be inserted therein, as illustrated in FIGS. 10-12. In other embodiments, however, the orientation and placement of the one or more target 122a, 122b, 122c can vary, such as being arranged in planar squares, rectangles, etc., or 3-dimensional cubes, pyramids, etc., and the wings 124, 126 can be placed elsewhere on or removed entirely from the calibration instrument 100. The calibration instrument 100 itself can also have various targets thereon, for example providing reference planes on one or more sides of the instrument 100, along edges thereof, etc. While the calibration instrument 100 has a specific rectangular wing structure illustrated in FIG. 1, in other embodiments, the calibration instrument can be any three-dimensional structure with one or more calibration reference elements thereon and one or more pivot points thereon.

While a variety of tracking approaches can be used, the targets 122a, 122b, 122c are configured to be captured in images and to provide orientation, location, and scale information based on their relative positions to each other in the images. For instance, if an image captures the targets 122a, 122b, 122c all in the triangular orientation visible by looking straight down on the calibration instrument 100, the calibration instrument 100 is oriented such that the calibration reference array 120 is facing directly at the monitoring system 200. If the targets 122a, 122b, 122c are captured such that all three targets are positioned along a shared line, the calibration instrument 100 is positioned such that the calibration reference array 120 is perpendicular to the monitoring system 200. Thus, as the calibration instrument 100 moves three-dimensionally while the calibration reference array 120 is within view of the monitoring system 300, the targets 122a, 122b, 122c allow the location, orientation, and scale within the image of the calibration instrument 100 to be determined by mapping the known and predetermined coordinates of the targets 122a, 122b, 122c relative to each other to the actual coordinates of the targets 122a, 122b, 122c in the captured images. A virtual representation of the calibration instrument 100 can thus be rotated and oriented so that the known and predefined orientations of the targets 122a, 122b, 122c on the virtual representation match up with the actual imaged targets 122a, 122b, 122c. The virtual representation of the calibration instrument can be a plurality of coordinates defining the shape of the calibration instrument 100 and stored in a memory, as discussed below. Because the calibration reference array 120 is attached to the calibration instrument 100 in a known orientation and because the shape and size of the calibration instrument 100 is known, the location and pose of the calibration instrument can be accurately determined. Once the orientation of the calibration reference array 120 is determined, the relative distances between the targets 122a, 122b, 122c in the actual image can be used for scale because the actual distances between the targets are known and predefined.

While FIG. 1 illustrates three targets 122a, 122b, 122c in the form of spheres, any number of targets can be used, and the targets can take various different forms, such as flat images, grids, geometric shapes, patterns, various transmitting elements, lights, etc. The targets 122a, 122b, 122c are configured to be passive targets, however active targets can be used in some embodiments requiring one or more power sources, such as light-emitting diodes (LEDs), or a combination of active and passive tracking can be used. In other embodiments, one or more various different sensors can be used as reference elements instead of or in addition to one or more of the targets 122a, 122b, 122c or instead of the calibration reference array 120 entirely, such as electromagnetic sensor(s), gyroscope(s), various radio-frequency identification (RFID) tags or various transmitting tags, etc. The calibration reference array 120 and the calibration instrument 100 can be made from a variety of different materials, such as medical grade metals, plastics, polymers, ceramics, etc.

Figure 3:
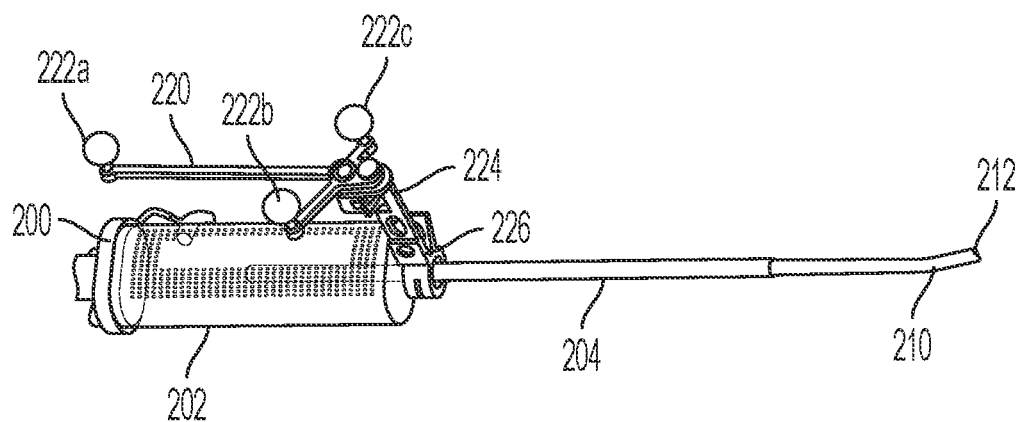
FIG. 3 is a perspective view of one embodiment of a surgical instrument.
Figure 4:
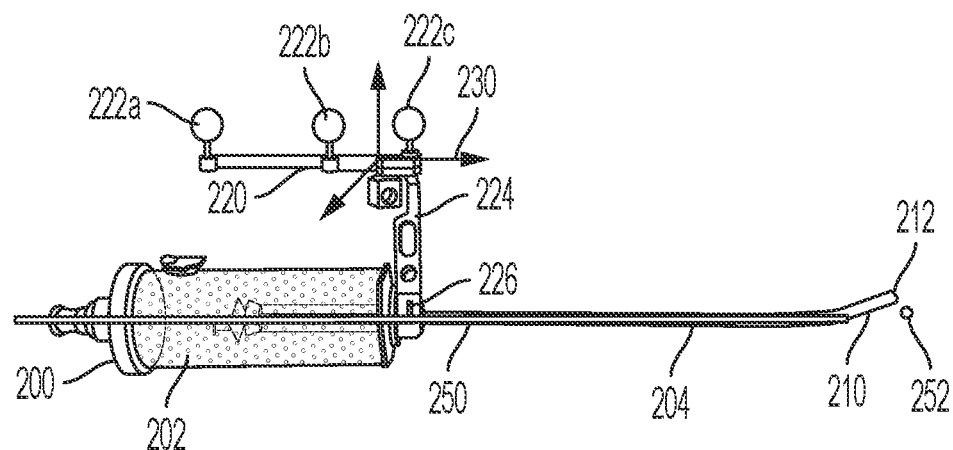
FIG. 4 is a perspective view of the surgical instrument of FIG. 3.

As indicated above, the pivot point 110 of the calibration instrument 100 is configured to receive a tip on a surgical instrument to allow a surgical instrument to be calibrated. FIGS. 3 and 4 illustrate one embodiment of a surgical instrument 200 that has an elongate shaft 204 extending from a handle 202 with a curved distal tip 210 on a distal end thereof. The surgical instrument 200 can be calibrated such that an accurate virtual representation of at least an axis of the elongate shaft 204 and the curved distal tip 210 can be generated by the monitoring system 300. The virtual representation of the surgical instrument 200 can be a plurality of data points, e.g., coordinates, that aid in defining the shape of the surgical instrument 200. The data points can be stored in a memory and updated in the memory based on the calculations discussed herein, as discussed in detail below.

The instrument 200 is configured to be calibrated through interaction with the calibration instrument 100 and the monitoring system 300. Calibration can be achieved by comparing measured data to predetermined data based on a predefined or ideal instrument axis 250 and a predefined or ideal instrument tip 252. The predefined instrument axis 250 and the predefined instrument tip 252 may not necessarily reflect a current configuration of the elongate shaft 204 and a distal-most end 212 of the instrument 200. Rather, they can be calculated based on the design and/or manufacturing parameters for the instrument. For example, the predetermined data can be in the form of one or more coordinates representing ideal locations of one or more reference arrays on an ideal instrument. The coordinates, referred to as predetermined instrument coordinates, represent initial or expected data that can be provided to the monitoring system 300 to generate an initial or expected virtual representation of the instrument 200. The initial or expected virtual representation can be used to calibrate a newly manufactured instrument and/or a used instrument. The predefined instrument axis 250 and the predefined instrument tip 252 can be specific to the type of instrument, and the values may be different when different instruments are used in other embodiments. While data representing the predefined instrument axis 250 and the predefined instrument tip 252 are provided to the monitoring system, a variety of other data can also be provided in some embodiments, such as instrument type, number of uses, etc.

By way of non-limiting example, the illustrated surgical instrument 200 is the DePuy Synthes Concorde Clear minimally invasive discectomy device, however a variety of instruments can be used, configured both for minimally-invasive or more traditional surgeries. The surgical instrument 200 can be made from a variety of different materials, such as medical grade metals, plastics, polymers, ceramics, etc. While the illustrated instrument 200 has a curved distal tip 210, an instrument with a straight distal tip can be used in other embodiments, such as instruments with sharp or pointed distal tips, screwdrivers, etc.

Similar to the calibration instrument 100, the surgical instrument 200 also has an orientation array 220 attached thereto that can be tracked by the monitoring system 300 and that has a predefined arrangement known to the monitoring system 300 such that it can provide predefined instruments coordinates within a predefined 3-dimensional instrument coordinate system 230 to the monitoring system 300 during calibration.

As the instrument 200 is calibrated by pivoting in the pivot point 110, the orientation array 220 allows the monitoring system 300 to take images containing the orientation array 220. Because the dimensional arrangement and orientation of the orientation array 220 is predefined and known to the monitoring system 300, the orientation array 220 allows the monitoring system 300 to use the orientation array 220 in each image as a reference scale to determine various orientation and measurement values of other objects in the images based on the position and visibility of the orientation array 220 in each image, such as the surgical instrument 200. Thus, the monitoring system 300 can effectively place other objects in the images to scale within the context of the instrument coordinate system 230.

Similar to the calibration reference array 120, in the illustrated embodiment the orientation array 220 has three targets 222a, 222b, 222c thereon that can be imaged and tracked by the monitoring system 300 to provide the instrument coordinate system 230 in a similar manner to the targets 122a, 122b, 122c of the calibration instrument 100 discussed above. The targets 222a, 222b, 222c are arranged in a generally triangular arrangement to one another in a single plane that extends parallel to and offset from a longitudinal axis of the surgical instrument 200. The orientation array 220 is coupled to the surgical instrument 200 in a known and predefined orientation by an orientation arm 224 with a predefined length and an orientation ring 226, however the orientation array 220 can be coupled to the instrument 200 in a variety of different ways.

Using the same imaging approach as the calibration reference array 120, the surgical instrument 200 moves three-dimensionally while the orientation array 220 is within view of the monitoring system 300. The targets 222a, 222b, 222c thus allow the location, orientation, and scale within the image of the surgical instrument 200 to be determined by mapping the actual imaged coordinates of the targets 222a, 222b, 222c in the captured images. The mapped coordinates of the targets 222a, 222b, 222c on the instrument 200, referred to herein as the measured instrument coordinates, can be compared to the predetermined instrument coordinates calculated based on an ideal instrument. The system 300 can use these coordinates to generate a virtual representation of the surgical instrument 200 such that the measured instrument coordinates of the targets 222a, 222b, 222c on the virtual representation overlay the predetermined instrument coordinates of actual imaged targets 222a, 222b, 222c. Because the orientation array 220 is attached to the surgical instrument 200 in a known orientation and because the shape and size of the surgical instrument 200 is known, the location and pose of the surgical instrument 200 with the curved distal tip 210 can then be determined. Once the orientation of the orientation array 220 is determined, the distances between the targets 222a, 222b, 222c in the actual image can be used for scale because the actual distances between the targets are known and predefined.

There are three targets 222a, 222b, 222c illustrated in FIGS. 3 and 4, and the targets 222a, 222b, 222c are in the form of spheres. However, any number of targets can be used, and the targets can take various different forms, such as flat images, grids, geometric shapes, patterns, various transmitting elements, lights, etc. The targets 222a, 222b, 222c can be passive targets, however active targets can be used in some embodiments requiring one or more power sources, such as light-emitting diodes (LEDs), or a combination of active and passive tracking can be used. In other embodiments, one or more various different sensors can be used as orientation elements instead of or in addition to one or more of the targets 222a, 222b, 222c or instead of the orientation array 220 entirely, such as electro-magnetic sensor(s), gyroscope(s), various radio-frequency identification (RFID) tags or various transmitting tags, etc. The orientation array 220 can be made from a variety of different materials, such as medical grade metals, plastics, polymers, ceramics, etc.

Figure 5:
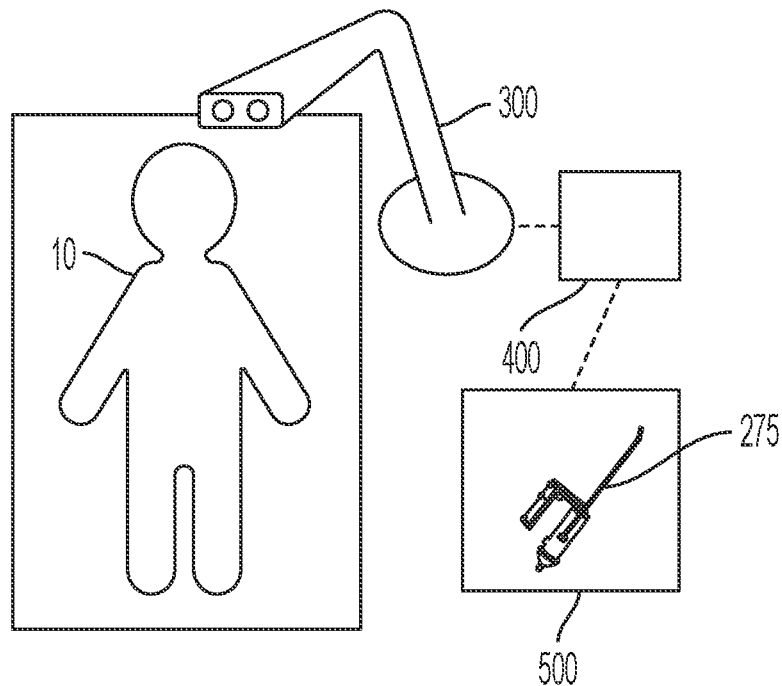
FIG. 5 is a top-down view of a patient and one embodiment of a monitoring system.

As noted, the calibration instrument 100 and/or the surgical instrument 200 can be tracked by a monitoring system, such as the monitoring system 300 illustrated in FIG. 5. Specifically, the monitoring system 300 is configured to track an orientation and a location of the configuration reference array 120 and the orientation array 220 relative to the monitoring system 300 during calibration of the surgical instrument 200, and it can be configured to track the surgical instrument 200 during use. For example, it is configured to track the targets 122a, 122b, 122c of the calibration instrument 100 and the targets 222a, 222b, 222c of the surgical instrument 200, as discussed in detail above, and it can be configured to record movement of the surgical instrument 200 when the curved distal tip 210 of the surgical instrument 200 is inserted into the pivot point 110 of the calibration instrument 100 and rotated thereabout, as discussed in detail below. Based on the recorded movement, e.g., the recorded coordinates, the monitoring system 300 can be configured to calculate a deviation of the curved distal tip 210 of the surgical instrument 200 from the predefined instrument tip 252. The monitoring system 300 can thus modify a virtual representation of the surgical instrument 200 on a surgical display, such as a virtual representation 275 of the surgical instrument 200 on a display 500 to be used during surgery on a patient 10 in FIG. 5, based on the calculated deviation such that the virtual representation accurately mirrors the actual curved distal tip 210 of the instrument 200 with any bends or deviations reflected therein. As discussed in detail below, this can be achieved in part by translating the measured instrument coordinates and predetermined instrument coordinates in coordinate system 230 onto coordinate system 130.

The monitoring system 300 can have a variety of configurations and can include various components, such as a navigation camera used for surgery. Depending on the type of target used, the monitoring system 300 can be configured to directly visualize the operating space through one or more cameras, and the monitoring system 300 can use active tracking, passive tracking, or some combination. It can also be part of a robotic surgical system, part of a computer-assisted surgical system, or a stand-alone device.

Figure 6:
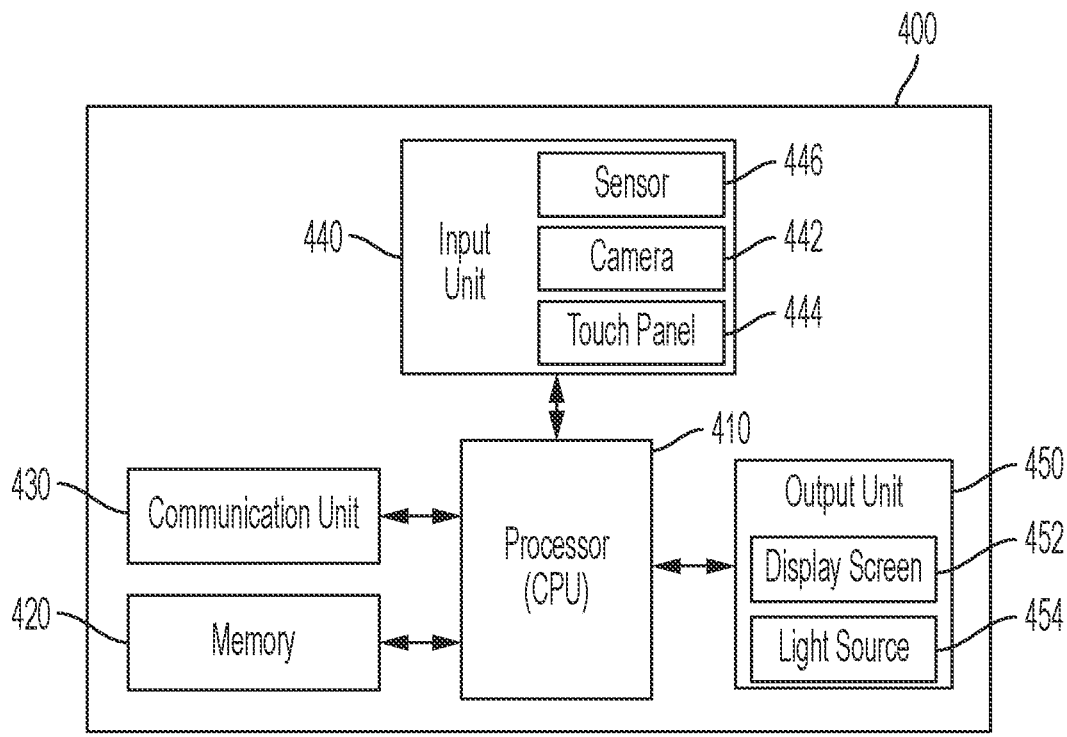
FIG. 6 is a diagram showing one embodiment of a control system architecture.

The control system or processor 400 is configured to assist in calculating the orientation and location of the arrays 120, 220 relative to the monitoring system 400 based on data gathered by the monitoring system 400. The control system 400 can be configured to calculate results both at a single point in time, periodically, or continuously over a period of time. The control system 400 can either be part of the monitoring system 300, can be part of a robotic surgical system, can be a separate component, or some combination of the preceding. In some embodiments, it can also communicate with at least one of the monitoring system 400, the calibration instrument 100 and/or the array 120, the surgical instrument 200 and/or the array 220, or some combination of the proceeding either directly or indirectly and either wirelessly or through wired connections. FIG. 6 illustrates a diagrammatic view of an exemplary device architecture of the control system 400.

As shown in FIG. 6, the control system 400 may contain multiple components, including, but not limited to, an internal processor (e.g., central processing unit (CPU) 410), a memory 420, a wired or wireless communication unit 430, one or more input units 440, and one or more output units 450. It should be noted that the architecture depicted in FIG. 6 is simplified and provided merely for demonstration purposes. The architecture of the control system 400 can be modified in any suitable manner as would be understood by a person having ordinary skill in the art, in accordance with the present claims. Moreover, the components of the control system 400 themselves may be modified in any suitable manner as would be understood by a person having ordinary skill in the art, in accordance with the present claims. Therefore, the device architecture depicted in FIG. 6 should be treated as exemplary only and should not be treated as limiting the scope of the present disclosure.

The internal processor 410 is capable of controlling operation of the control system 400 and/or the monitoring system 300 depending on whether the control system 400 and the monitor system 300 are combined or separate. More specifically, the processor 410 may be operable to control and interact with multiple components associated with the control system 400, as shown in FIG. 6. For instance, the memory 420 can store program instructions that are executable by the internal processor 410 and data. The process described herein may be stored in the form of program instructions in the memory 420 for execution by the internal processor 410. The communication unit 430 can allow the control system 400 to transmit data to and receive data from one or more external devices via a communication network. The input unit 440 can enable the control system 400 to receive input of various types, such as audio/visual input, user input, data input, and the like. To this end, the input unit 440 may be composed of multiple input devices for accepting input of various types, including, for instance, one or more cameras 442 (i.e., an imaging device), touch panel(s) 444, microphone(s) (not shown), sensors 446, one or more buttons or switches (not shown), and so forth. The input devices included in the input 440 may be manipulated by a user. Notably, the term image acquisition unit, as used herein, may refer to the camera 442, but is not limited thereto. For example, the image acquisition unit can be the monitoring system 300 or a part thereof. The output unit 450 can display information on the display screen 452 for a user to view. The display screen 452 can also be configured to accept one or more inputs, such as a user tapping or pressing the screen 452, through a variety of mechanisms known in the art, and the output unit 450 may further include a light source 454. In some embodiments, the output unit 450 can be configured to send any processing results to various systems, such as a robotic surgical system or a computer-assisted surgical system. The control system 400 and/or the monitoring system 300 can also be configured to calculate orientations of instruments, distances, translations of coordinate systems, etc. based on information from the arrays 120, 220.

Figure 7:
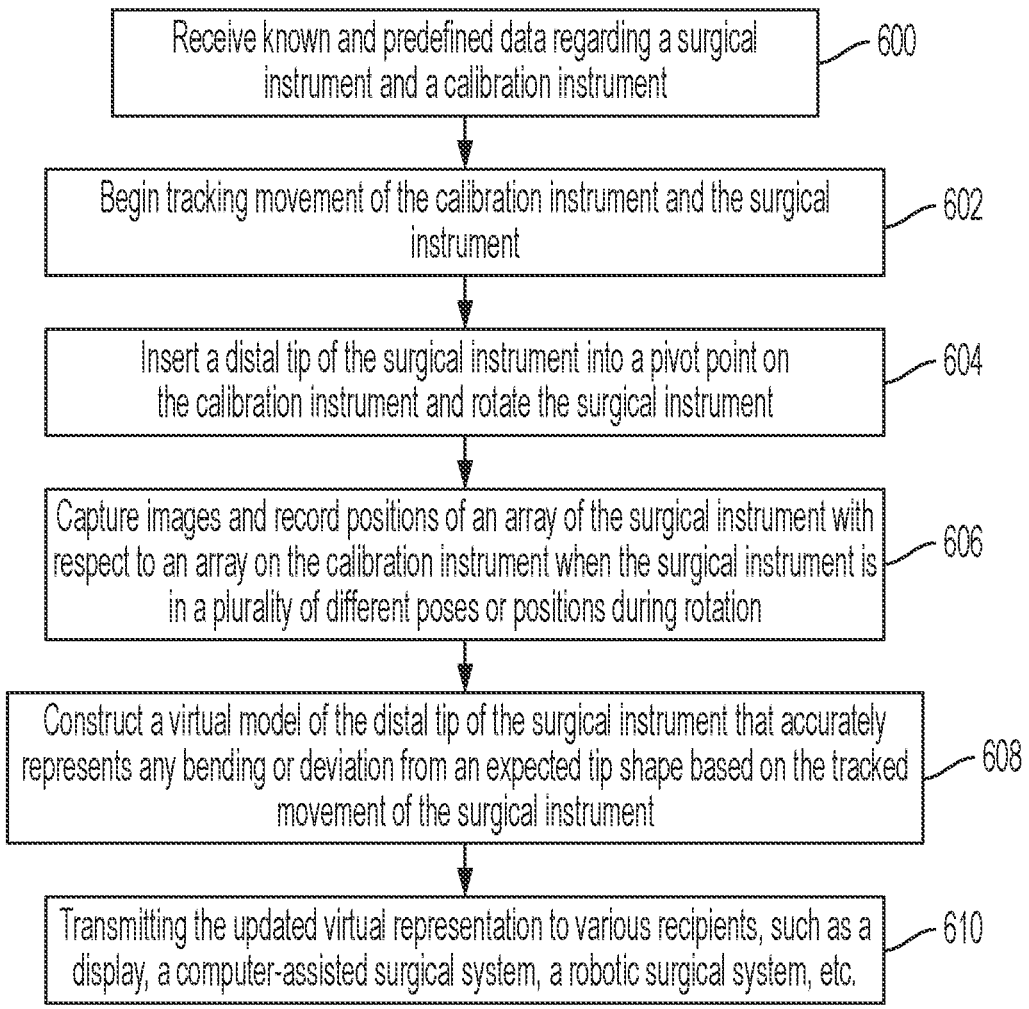
FIG. 7 illustrates a flow diagram of one embodiment of a calibration process of the surgical instrument of FIG. 3 rotating and/or pivoting with respect to the calibration instrument of FIG. 1.
Figure 8:
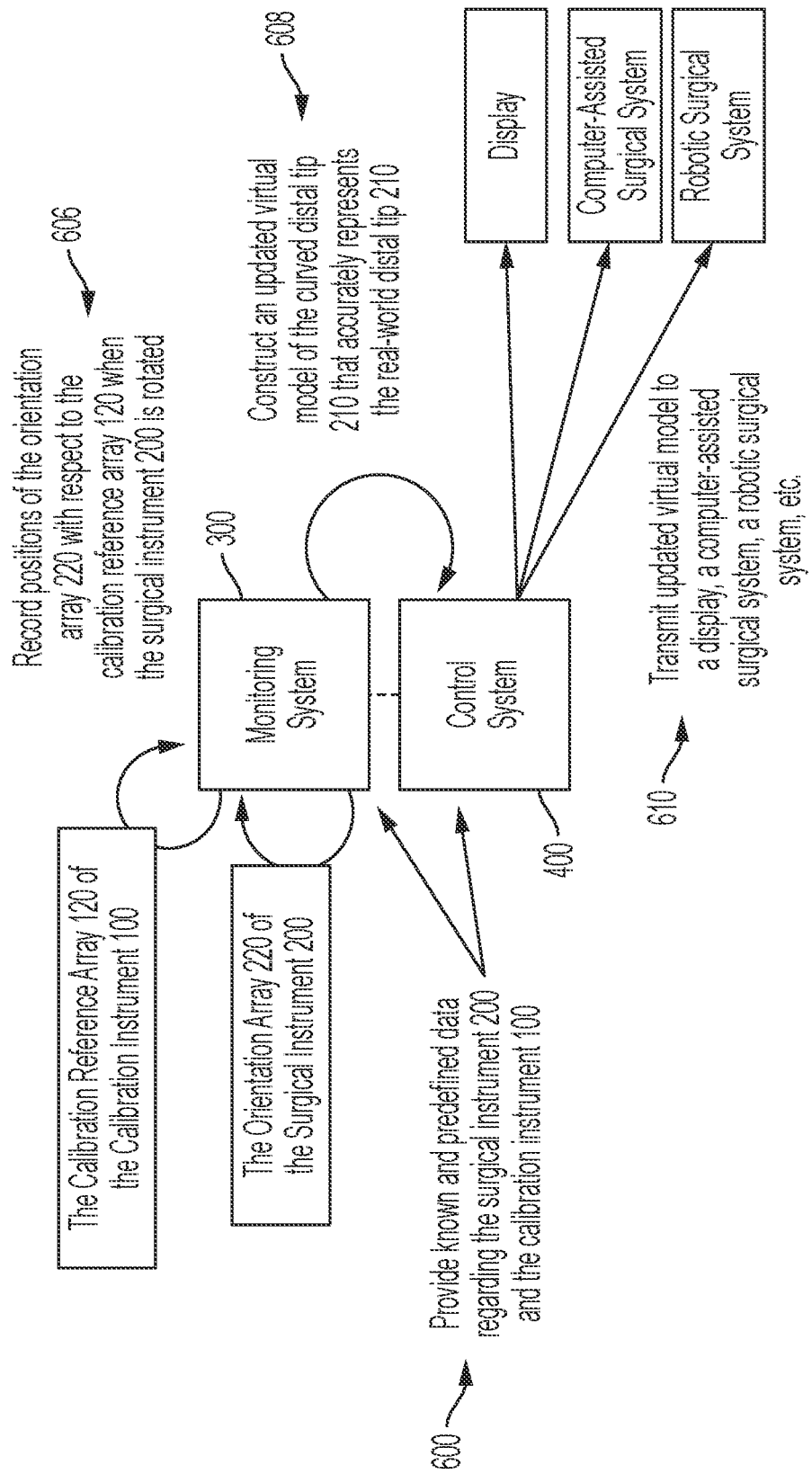
FIG. 8 illustrates another flow diagram of the calibration process of the instrument of FIG. 3.

As noted above, interaction of the calibration instrument 100, the surgical instrument 200, the monitoring system 300, and the control system 400 can allow the monitoring system 300 and/or the control system 400 to calculate a deviation of the curved distal tip 210 of the surgical instrument 200, and to modify the virtual representation of the surgical instrument 200 on a surgical display based on the calculated deviation. As illustrated at step 600 in FIGS. 7 and 8, initially, the monitoring system 300 and/or the control system 400 is provided with various known and predefined data as discussed above, such as a virtual representation of the surgical instrument 200 with the predefined instrument axis 250, the predefined instrument tip 252, and information regarding the orientation and arrangement of the orientation array 220 on the surgical instrument 200, which can all be represented by a plurality of data points (e.g., predetermined instrument coordinates) defining the shape and orientation of the surgical instrument with the predefined shaft and tip; and a virtual representation of the calibration instrument 100 with a known shape and size and information regarding the orientation and arrangement of the calibration reference array 120 on the calibration instrument 100, which can be represented by a plurality of data points defining the shape and orientation of the calibration instrument. This information can be provided through a variety of means, such as being manually inputted, automatically loaded by, for example, scanning or imaging one or more of the instruments 100, 200 and/or the arrays 120, 220 that can have identifying information thereon, downloaded onto the system 300, etc. The monitoring system 300 is initiated to begin tracking the calibration instrument 100 and the surgical instrument 200 at step 602, for example each instrument 100, 200 and/or each array 120, 220 can be displayed to the monitoring system 300 or the monitoring system 300 can be instructed manually to initiate tracking.

Figure 9:
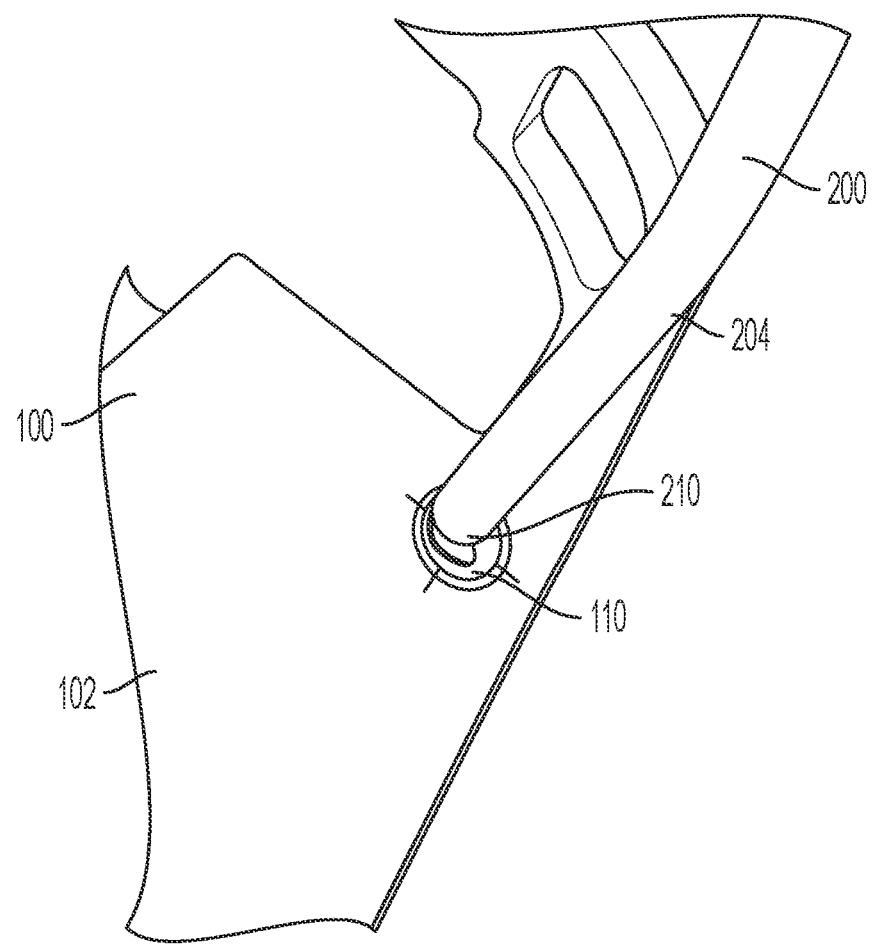
FIG. 9 is a perspective view of the surgical instrument of FIG. 3 interacting with the calibration instrument of FIG. 1.

The curved distal tip 210 of the surgical instrument 200 is inserted into the pivot point 110 of the calibration instrument 100 at step 604 and FIG. 9, for example by tipping the calibration instrument 100 at a defined angle as illustrated in FIGS. 10-12 and inserting the distal-most end 212 into the pivot point 110. The surgical instrument 200 is rotated in an approximately circular motion above the calibration instrument, as illustrated in FIGS. 10-12, and the monitoring system 300 records the movement of the orientation array 220 on the surgical instrument 200 relative to the fixed position of the calibration reference array 120 on the calibration instrument 100. As the surgical instrument 200 moves, the distal-most end 212 of the curved distal tip 210 remains in the cavity of the pivot point 110 because the pivot point 110 is sized and shaped to secure the distal-most end 212 therein while allowing the surgical instrument 200 to smoothly rotate and pivot. The pivot point 110 thus provides a fixed, known point about which the surgical instrument 200 can rotate. The monitoring system 300 thus captures images and records coordinates of the orientation array 220 when the surgical instrument 200 is in a plurality of different poses or positions at step 606. For example, FIGS. 10-12 illustrate exemplary rotation of the surgical instrument 200 while the monitoring system 300 captures a variety of images of the orientation array 220 in relation to the calibration reference array 120. As such, the rotation generally defines a circular shape 240 of movement above the pivot point 110 that corresponds to a path of motion of the orientation array 220.

The monitoring system 300 and/or the control system 400 can use the captured movement of the orientation array 220 (e.g. the measured instrument coordinates) in relation to the fixed pivot point 110 and the calibration reference array 120 to update the virtual representation of the surgical instrument 200. The system(s) 300/400 can do this by comparing the captured calibration movement (e.g. the measured instrument coordinates) to expected calibration movement (e.g. predetermined instrument coordinates) of a model of the surgical instrument 200 with the predefined instrument axis 250 and the ideal tip 252, discussed below.

Figure 13A:
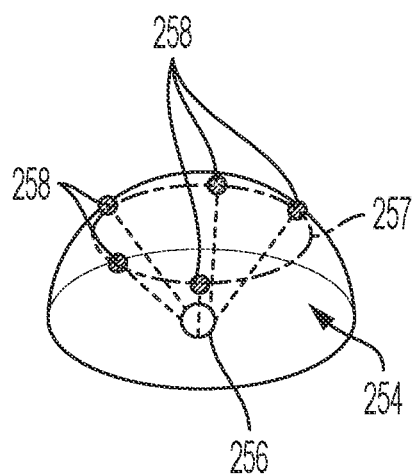
FIG. 13A is an image of a graphical interface showing a virtual sphere fit to a predefined or ideal version of the instrument of FIG. 3.

The monitoring system 300 and/or the control system 400 can be initially provided with data representing a model of the surgical instrument 200 with the predefined instrument axis 250 and the ideal tip 252. The system(s) 300/400 can also be provided with expected calibration movement data (e.g. predetermined instrument coordinates) of the surgical instrument 200 with the predefined instrument axis 250 and the ideal tip 252. However, in some embodiments, the system(s) 300/400 can also model the expected behavior itself using the predefined instrument axis 250 and the ideal tip 252 data. With a new or ideal instrument, calibration movement data is modeled based on technical diagrams of the instrument. In other embodiments, though, it can be directly measured and recorded on a never-before-used instrument. Expected calibration movement data can be modeled by assuming the ideal instrument is rotated in a manner similar to the instrument 200 about a fixed point 256. As such, a circle 257 of movement is defined above the fixed pivot point 256, as illustrated in FIG. 13A, that corresponds to a path of motion of an orientation array if the orientation array was fixed to the ideal instrument. For example, a plurality of points 258 can represent a plurality of coordinates of the ideal orientation array during calibration movement. The predefined instrument axis 250 defines a distance away from the fixed pivot point 256 at which the ideal orientation array would move, with each of the points 258 being positioned at the same distance away from the fixed point 256. Thus, movement of the ideal surgical instrument about the pivot point 256 with the ideal tip 252 inserted therein can define a semi-sphere 254 with the predefined instrument axis 250 acting as a radius of the sphere 254 and the fixed point 256 representing both a center of the semi-sphere 254 and a location of a distal-most tip of the ideal surgical instrument. The semi-sphere 254 can thus represent calibration movement data (e.g. predetermined instrument coordinates) of an ideal surgical instrument with the predefined instrument axis 250 and the ideal tip 252, and the center 256 of the semi-sphere can represent a location in 3-dimensional space of the distal-most end of the ideal tip 252. While steps to actually create such a model are discussed above, in some embodiments the calibration movement data (e.g. predetermined instrument coordinates) can be provided initially such that no extensive modeling of an ideal surgical instrument is required.

Figure 13B:
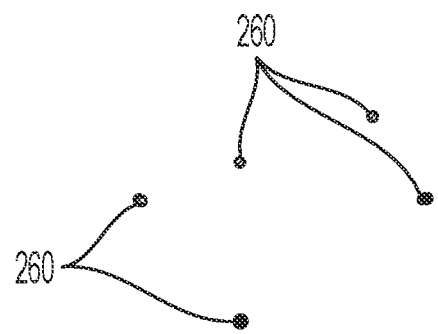
FIG. 13B is an image of a graphical interface showing virtual tracking points created based on the rotation of FIGS. 10-12.
Figure 13C:
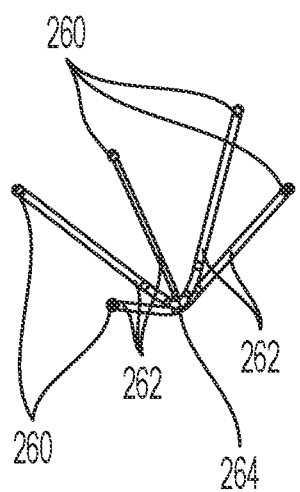
FIG. 13C is an image of a graphical interface showing virtual instrument shafts of the instrument of FIG. 3 based on the tracking points of FIG. 13B.
Figure 13D:
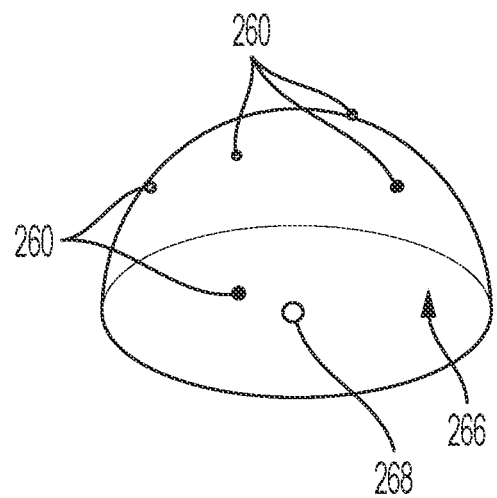
FIG. 13D is an image of a graphical interface showing a virtual sphere fit to the tracking points of FIG. 13B.

Returning to the surgical instrument 200, the circular shape 240 of movement of the surgical instrument 200 above the pivot point 110 represents similar motion to the circle 257 of movement above the fixed pivot point 256 that defines ideal or predefined motion of an ideal version of the surgical instrument. The circular shape 240 of movement of the surgical instrument 200 is defined by data points 260 captured by the monitoring system 300 of movement of the orientation array 220. The points 260 illustrated in FIG. 13B represent coordinates of movement of the orientation array 220 (and thus of the surgical instrument 200) in 3-dimensional space with respect to the pivot point 110 during calibration. The data points 260 thus represent similar coordinates to the points 258 that define ideal orientation array movement during calibration. As such, the points 260 can be used to model virtual representations 262 of the elongate shaft 204 of the surgical instrument 200 in a plurality of poses corresponding to a plurality of poses of the elongate shaft 204 during actual pivoting, as illustrated in FIG. 13C. The virtual representations 262 can be determined because they extend from the points 260, which represent movement of the orientation array 220 of the instrument 200, and they terminate in a common virtual distal tip 264, which represents the curved distal tip 210 as it pivots in the pivot point 110. During pivoting, the recorded points 260 are all at a same distance away from the pivot point 110 because an overall length of the elongate shaft 204 of the instrument 200 does not change during calibration. This is similar to the ideal surgical instrument in which the predefined instrument axis 250 defines a distance away from the fixed pivot point 256 at which the points 258 are positioned in the ideal instrument. The monitoring system 300 and/or the control system 400 can then mathematically match a semi-sphere 266 to the recorded points 260, as illustrated in FIG. 13D and similar to the semi-sphere 254 of the ideal instrument. Movement of the actual surgical instrument 200 and recorded points 260 may not represent a perfect semi-sphere because measurements are being made in an actual operating setting and the curved distal tip 210 may be warped or bent. The semi-sphere 266 can thus be a best-fit sphere to the points 260, and the predefined instrument axis 250 can be used as an initial sphere radius to help determine a sphere fit if needed. A center 268 of the semi-sphere 266 represents a location of the distal-most end 212 of the curved distal tip 210 because it was stationary in the pivot point 110 while the instrument 200 pivoted about that point. This is similar to the fixed point 256 representing both the center of the ideal semi-sphere 254 and the location of the distal-most tip of the ideal surgical instrument. The center 268 can thus correspond to the actual curved distal tip 210 with any warping or bending thereon.

Figure 13E:
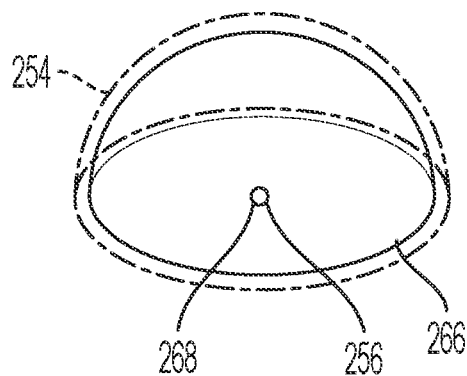
FIG. 13E is an image of a graphical interface showing the virtual sphere of FIG. 13D mapped or transposed onto the virtual sphere of FIG. 13A.
Figure 14:
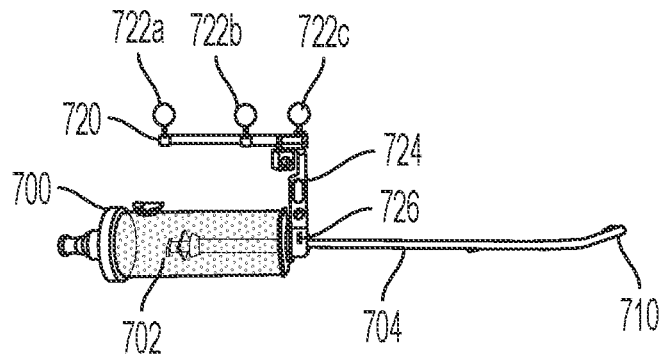
FIG. 14 is a perspective view of another embodiment of a surgical instrument.

The monitoring system 300 and/or the control system 400 can then map or transpose the semi-sphere 266 of the actual curved distal tip 210 onto the ideal semi-sphere 254 of the ideal tip 252, as illustrated in FIG. 13E. The system(s) 300, 400 can compare the semi-spheres 254, 266 to one another while placing the centers 268, 256 of the semi-spheres 254, 266 at a same or shared coordinate point. The centers 268, 256 of the semi-spheres 254, 266 can be placed at the same coordinate point because they represent the pivot point 110 and the fixed point 256 about which the surgical instrument 200 and the ideal surgical instrument were pivoted. If the semi-spheres 254, 266 correspond perfectly relative to each other, then the system(s) 300, 400 can determine that there is no warping or bending of the distal tip 210 from the ideal tip 252 because there is no deviation between the semi-spheres 254, 266. If there is any deviation between the two semi-spheres 254, 266, the monitoring system 300 and/or the control system 400 can determine that there is bending or warping in the distal tip 210 because calibration motion of the surgical instrument 200 does not correspond exactly to that of an instrument with the ideal tip 252. Additionally, the amount of deviation can be determined because these spheres 254, 266 are modeled in the same 3-dimensional coordinate system 130. As such, any deviation of the measured semi-sphere 266 (representing the measured instrument coordinates) from the ideal semi-sphere 254 (representing the predetermined instrument coordinates) thus correlates to any bending or warping of the actual curved distal tip 210 from the ideal distal tip 252. This correlated deviation can then be used to update the virtual model of the curved distal tip 210 to more accurately represent any bending or warping measured during calibration. As one illustrative example, the ideal semi-sphere 254 has a larger radius than the illustrated measured semi-sphere 266 in FIG. 13E. As such, this deviation indicates that the curved distal tip 210 has been bent toward the orientation array 220, which reduces a distance between the distal tip 210 and the orientation array 220 and thus causes a shorter or smaller radius of the measured semi-sphere 266. Based on the amount of deviation between the radius of the ideal semi-sphere 254 and the radius of the measured semi-sphere 266, the degree or amount by which the curved distal tip 210 has been bent toward the orientation array 220 can be determined. Once any deviation is calculated, the system(s) 300, 400 can update the virtual model of the curved distal tip 210 so that it accurately represents the 3-dimensional location of its distal-most end 212 with any bending or warping at step 608. The updated virtual model provides a more accurate representation of the surgical instrument 200, providing better surgical results to a surgeon because the instrument 200 can be accurately represented while also not requiring disposal of a surgically-acceptable instrument because of minor bending. The updated virtual model can also be created through a single-step process of rotating the surgical instrument 200 in the pivot point 110 rather than any multi-stage process involving multiple measurements and calibration instruments.

The monitoring system 300 and/or the control system 400 can provide the updated virtual representation of the surgical instrument 200 with any warping of the curved distal tip 210 in step 610 to the surgeon and/or a surgical system through a variety of means, for example by being displayed on various displays for the surgeon, by being modeled as a virtual 3-dimensional image in real time, by being provided to a computer-assisted surgical system, by being provided to a robotic surgical system, etc. As illustrated in FIG. 5, updating a virtual representation of the surgical instrument 200 with any warping of the curved distal tip 210 can thus include updating the virtual representation 275 of the surgical instrument 200 with the plurality of data points defining the shape and orientation of the surgical instrument 200 and the curved distal tip 210 by saving new values of the plurality of data points based on the calculated deviation to a memory, such as the memory 420 of the control system 400. As noted above, the monitoring system 300 and/or the control system 400 can be directly incorporated into various computer-assisted surgical systems and/or robotic surgical systems in other embodiments. In some embodiments, the surgeon can then perform an operation, such as a minimally-invasive surgery, on a patient using the updated virtual representation 275 of the surgical instrument 200. The calibration process discussed herein can be repeated as needed, and the predefined and/or ideal values discussed herein can represent either values from instruments that have not experienced any bending or warping or values from previously-performed calibration processes that represent some previous bending or warping but may need to be updated for continued accurate use.

FIGS. 14-17B illustrate another embodiment of a surgical instrument 700 similar to the surgical instrument 200 with an elongate shaft 704 extending from a handle 702 and a curved distal tip 710 on a distal end of the elongate shaft 704. Like surgical instrument 200, surgical instrument 700 can be calibrated such that an accurate virtual representation of at least an axis of the elongate shaft 704 and the actual curved distal tip 710 can be generated that accurately reflects bends or distortions of the curved distal tip 710 and provided to a computer or robotic surgical system, such as the monitoring system 300. The instrument 700 can be calibrated through interaction with the calibration instrument 100 and the monitoring system 300.

Figure 15:
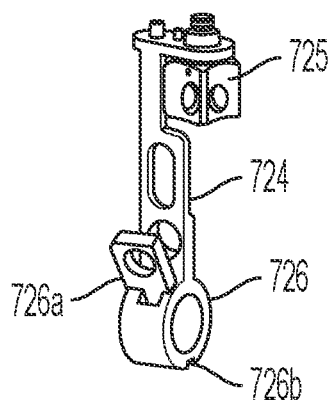
FIG. 15 is a perspective view of an orientation arm of the surgical instrument of FIG. 14.
Figure 16:
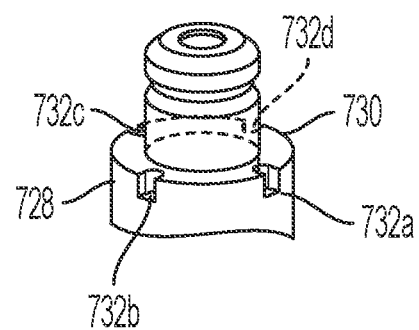
FIG. 16 is a perspective view of a ring coupling of the surgical instrument of FIG. 14.
Figure 17A:
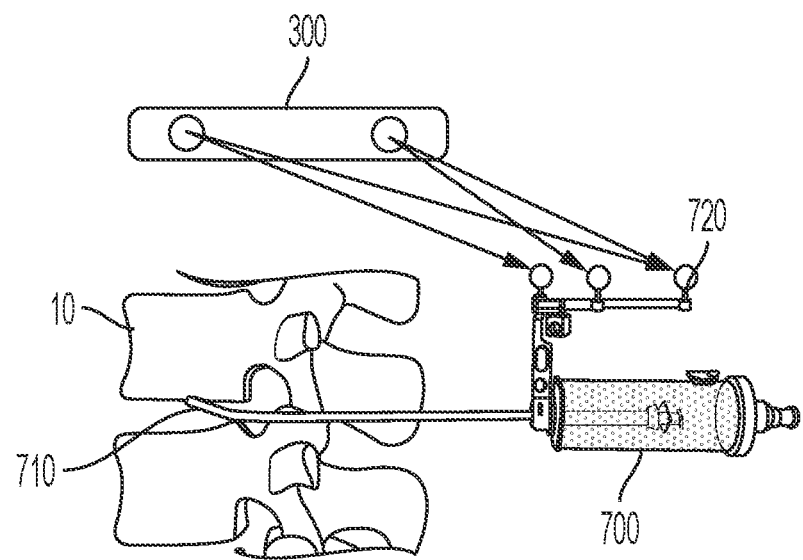
FIG. 17A is a perspective view of the surgical instrument of FIG. 14 in use.
Figure 17B:
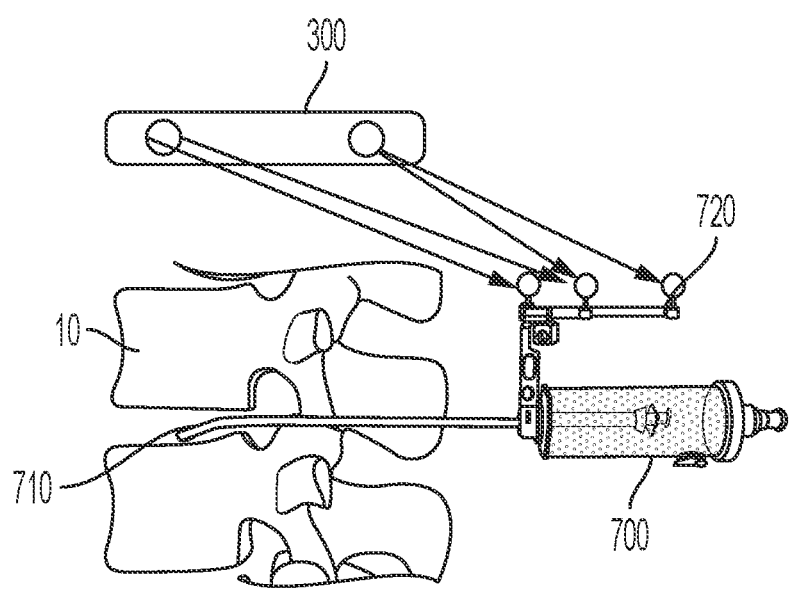
FIG. 17B is a perspective view of the surgical instrument of FIG. 14 in use.

The surgical instrument 700 has an orientation array 720 attached thereto, similar to array 220, that can be tracked by the monitoring system 300, similar to arrays 120, 220 discussed in detail above, and to have a predefined arrangement known to the monitoring system 300 such that it can provide a predefined 3-dimensional instrument coordinate system, similar to the coordinate system 230. However, while the orientation array 220 is configured to remain in one fixed orientation after calibration, the orientation array 720 can be rotated to a predefined plurality of different known orientations during use without requiring recalibration by the monitoring system 300 and the calibration instrument 100. Because the plurality of different known orientations are provided to the monitoring system 300 during initial calibration, the monitoring system 300 and/or the control system 400 can be configured to determine an orientation and update a virtual representation of the surgical instrument 700 during use when the orientation array 720 is moved into a different one of the plurality of known orientations than the one used during initial calibration. The surgical instrument 700 can therefore be configured for use in a plurality of different orientations with the curved distal tip 710 being rotated as needed during surgery while being able to rotate the orientation array 720 to one of the plurality of different known orientations to ensure the orientation array 720 is still visible to the monitoring system 300 without blocking the view and without having to recalibrate the instrument 700, as illustrated in FIGS. 17A and 17B. For example, the orientation array 720 has three targets 722a, 722b, 722c thereon that can be imaged in a similar manner to the targets 122a, 122b, 122c and the targets 222a, 222b, 222c. The orientation array 720 is coupled to the surgical instrument 700 in one of four known and predefined orientations by engaging an array interface 725 at one end of an orientation arm 724 with a predefined length that has an orientation ring 726 disposed at an opposite end, as illustrated in FIG. 15. The orientation ring 726 couples onto the instrument 700 through engagement with a ring coupling 728 disposed at a proximal end of the handle 702, and as illustrated in FIG. 16, the ring coupling 728 has a generally circular engagement surface 730 that is configured to interact with the ring coupling 728 of the orientation array 720 and has four notches 732a, 732b, 732c, 732d formed therein. The orientation ring 726 interacts with the four notches 732a, 732b, 732c, 732d such that the orientation ring 726 can engage with each notch in turn and remain in a temporarily-fixed orientation with respect to the surgical instrument 700 with respect to one of the notches 732a, 732b, 732c, 732d. For example, it can have four corresponding protuberances (not shown) on an inner surface of the orientation ring 726 that are configured to engage the four notches 732a, 732b, 732c, 732d. The ring 726 can also be opened by an engagement mechanism 726a and a hinge 726b such that the orientation ring 726 can be opened, rotated, and reengaged with the notches as desired. In use, the orientation ring 726, and thus the orientation array 720 extending therefrom, can engage with the notch 732a during calibration and initial use such that the orientation array 720 is visible to the monitoring system 300, as illustrated in FIG. 17A. However, during use, the orientation ring 726 can be disengaged from the notch 732a and rotated 180 degrees about the elongate shaft 704 of the surgical instrument 700 and to reengage the ring coupling 728 at the notch 732c, thus rotating the orientation array 720 coupled thereto around to an opposite side of the surgical instrument 700 during use, as illustrated in FIG. 17B. Because of this rotation, the curved distal tip 710 of the surgical instrument 700 can be applied to a different boney structure in a patient while the orientation array 720 can remain visible to the monitoring system 300 to allow continued tracking. While four notches 732a, 732b, 732c, 732d are illustrated herein, any number and type of engagement point is possible to allow an orientation array to be rotated to a predefined plurality of different known orientations.

Calibration of the instrument 700 is performed through the same process as instrument 200 discussed above, which involves rotation in the pivot point 110 of the calibration instrument 100 and tracking of the monitoring system 300 to generate an accurate virtual representation of the surgical instrument 700 and the curved distal tip 710. However, monitoring system 300 and/or the control system 400 is provided with the predefined plurality of different known orientations of the orientation array 720, such as four in the illustrated embodiment, and each orientation is uniquely identified, such as orientations in notches 732a, 732b, 732c, 732d. As the orientation is changed during use, as illustrated in FIGS. 17A and 17B when the instrument 700 is used on vertebra of the patient 10, the monitoring system 300 and/or the control system 400 is provided with the unique identifier of the new orientation so that the monitoring system 300 and/or the control system 400 can determine a new location and pose of the surgical instrument 700 and its curved distal tip 710 based on the new designated orientation, such as when the orientation array 720 is moved from the orientation in notch 732a in FIG. 17A to the orientation in notch 732c in FIG. 17B. Because the monitoring system 300 and/or the control system 400 knows the fixed orientations at notches 732a, 732b, the monitoring system 300 and/or the control system 400 can update a virtual representation of the overall orientation or pose of the surgical instrument 700 without having to recalibrate the instrument 700, for example by updating a plurality of data points of the virtual representation defining the surgical instrument 700. After changing the orientation of the orientation array 720, the identity of the new designated orientation can be provided to the monitoring system 300 and/or the control system 400 during use in a variety of ways. For example, the instrument 700 can have various markings, flags, sensors, engagements, patterns, etc. on the handle 702, the shaft 704, the orientation ring 726, the ring coupling 728, etc. that can either electronically or visually indicate to the monitoring system 300 and/or the control system 400 the change. The information can also be input to the monitoring system 300 and/or the control system 400 manually, such as by the surgeon or an assistant.

Figure 18:
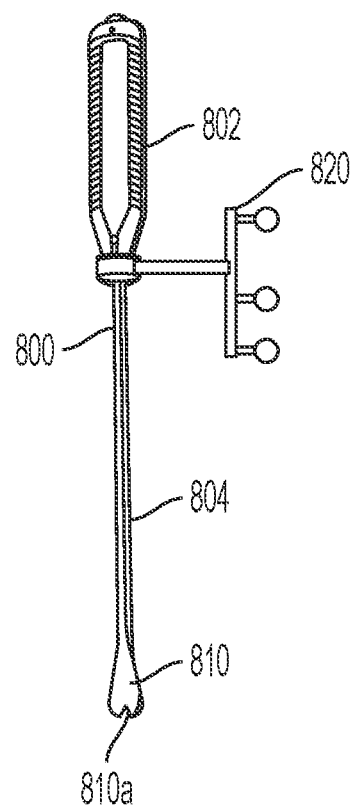
FIG. 18 is a side view of another embodiment of a surgical instrument.
Figure 19:
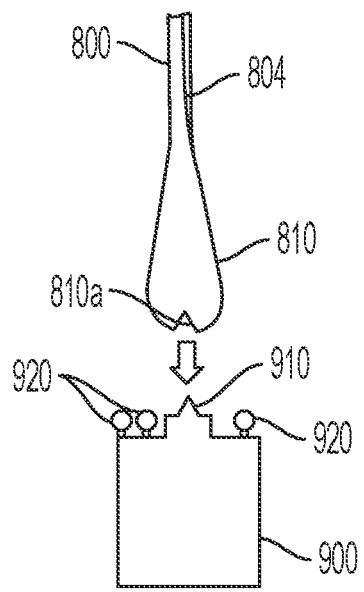
FIG. 19 is a side view of a distal end of the surgical instrument of FIG. 18 with another embodiment of a calibration instrument.
Figure 20:
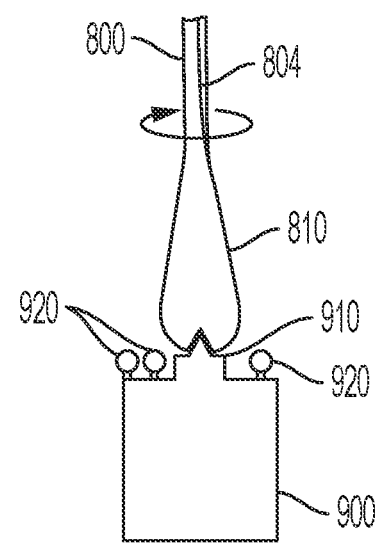
FIG. 20 is a side view of the distal end of the surgical instrument of FIG. 18 with the calibration instrument of FIG. 19.

While instruments with protruding distal-most tips have been illustrated, in other embodiments, instruments having a cavity or void at a distal end thereof can also be calibrated with a calibration instrument having a protuberance, cone, sphere, etc. for using the same method as discussed above. FIGS. 18-20 illustrate a surgical instrument 800 similar to instruments 200, 700. The surgical instrument 800 has an elongate shaft 804 extending from a handle 802 and a straight distal tip 810 having a cavity 810a defined therein on a distal end of the elongate shaft 804. The cavity 810a is in the shape of an inverse cone, however a variety of different instruments with different cavities can be used, such as oval, semi-spherical, cylindrical, curved, etc. The surgical instrument 800 has an orientation array 820 attached thereto, similar to arrays 220, 720, that can be tracked by the monitoring system 300. Thus, surgical instrument 800 can be calibrated similar to surgical instruments 200, 700 such that an accurate virtual representation of at least an axis of the elongate shaft 804 and the actual distal tip 810 can be generated that accurately reflects any bends or distortions of the distal tip 810 and can be provided to a computer or robotic surgical system, such as the monitoring system 300.

Furthermore, the instrument 800 can be calibrated through interaction with a calibration instrument 900, similar to calibration instrument 100. The calibration instrument 900 has a calibration reference array 920 thereon, similar to array 110, that can be tracked by the monitoring system 300. The instrument 900 also has a pivot point 910, similar to pivot point 110, about which the instrument 800 can be pivoted and rotated for calibration, similar to the calibration process discussed above. The pivot point 910 protrudes from an upper surface of the calibration instrument 900 and is in the shape of a cone that is inserted into the cavity 810a of the distal tip 810 on the instrument 800, as illustrated by the arrow in FIG. 19. However, any protruding shape can be used to correspond to a particular cavity on a surgical instrument to be calibrated, such as semi-spheres, cylinders, prisms, etc. Once the distal tip 810 of the surgical instrument 800 is engaged with the calibration instrument 900, the instrument 800 is rotated thereabout for calibration, as illustrated by the arrow in FIG. 20 and similar to the process discussed above.

All of the devices disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It is preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Additionally, it is understood that one or more of the systems and methods herein, or aspects thereof, may be executed by at least one processor. The processor may be implemented in various devices, as described herein. A memory configured to store program instructions may also be implemented in the device(s), in which case the processor can be specifically programmed to execute the stored program instructions to perform one or more processes, which are described further herein. Moreover, it is understood that the methods may be executed by a specially designed device, a mobile device, a computing device, etc., comprising the processor, in conjunction with one or more additional components, as described in detail herein.

Furthermore, the systems and methods, or aspects thereof, of the present disclosure may be embodied as non-transitory computer readable media on a computer readable medium containing executable program instructions executed by the processor. Examples of the computer readable mediums include, but are not limited to, ROM, RAM, compact disc (CD)-ROMs, magnetic tapes, floppy disks, flash drives, smart cards, and optical data storage devices. The computer readable recording medium can also be distributed in network-coupled computer systems so that the computer readable media is stored and executed in a distributed fashion, for example by a cloud-based system, a telematics server, a Controller Area Network (CAN), etc.

One skilled in the art will appreciate further features and advantages of the described devices and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. An instrument calibration system, comprising:
   a surgical instrument having an elongate shaft with a proximal end and a distal end, the distal end having a distal tip, the proximal end having an orientation element fixed in an initial position thereon;
   a calibration instrument having a pivot point thereon configured to receive the distal-most tip of the surgical instrument for pivoting thereabout, the calibration instrument having a predefined geometric structure and a calibration reference element attached thereto; and
   a monitoring system configured to map coordinates of the orientation element relative to the calibration reference element as the surgical instrument is moved with the distal-most tip of the surgical instrument positioned at the pivot point of the calibration instrument, the monitoring system being configured to calculate a deviation of the mapped coordinates of the orientation element from a plurality of corresponding reference coordinates of a predefined surgical instrument according to manufacturing parameters and having a predefined distal tip, and being configured to modify, based on the calculated deviation, a virtual representation of the predefined surgical instrument on a display to depict a virtual representation of the surgical instrument, wherein the mapped coordinates of the orientation element and the plurality of corresponding reference coordinates are characterized by respective first and second semi-spheres, and wherein the calculated deviation corresponds to a difference in form between the first and second semi-spheres.

2. The instrument calibration system of claim 1, wherein the distal tip is curved.

3. The instrument calibration system of claim 1, wherein the calculated deviation corresponds to a degree of curvature in the distal tip.

4. The instrument calibration system of claim 1, wherein a calculated deviation corresponds to a curve in a distal-most tip of the surgical instrument.

5. The instrument calibration system of claim 1, wherein the monitoring system is configured to determine an initial orientation of the orientation element with respect to the surgical instrument while the orientation element remains in a fixed position relative to the surgical instrument.

6. The instrument calibration system of claim 5, wherein the monitoring system is configured to determine an actual orientation of the surgical instrument while the orientation element on the proximal end thereof is moved to one of a plurality of second positions different than the initial position.

7. The instrument calibration system of claim 1, wherein the pivot point of the calibration element comprises a plurality of removable and replaceable pivot points.

8. The instrument calibration system of claim 7, wherein each of the plurality of removable and replaceable pivot points corresponds to a different type of distal tip usable with the surgical instrument.

9. The instrument calibration system of claim 1, wherein the pivot point protrudes from the calibration element, and wherein the distal tip has a corresponding cavity shaped and sized to receive the protruding pivot point.

10. The instrument calibration system of claim 1, wherein the orientation element can be configured to move to a plurality of secondary positions from the fixed initial position.

11. The instrument calibration system of claim 10, wherein the monitoring system is configured to identify the plurality of secondary positions of the orientation element.

12. The instrument calibration system of claim 10, wherein the monitoring system is configured to update the virtual representation to correspond to one of the plurality of secondary positions.

* * * * *